US010752938B2

(12) United States Patent
Chun et al.

(10) Patent No.: US 10,752,938 B2
(45) Date of Patent: *Aug. 25, 2020

(54) DETECTION OF A TARGET NUCLEIC ACID SEQUENCE USING TWO DIFFERENT DETECTION TEMPERATURES

(71) Applicants: SEEGENE, INC., Seoul (KR); Jong Yoon Chun, Seoul (KR); Young Jo Lee, Seoul (KR)

(72) Inventors: Jong Yoon Chun, Seoul (KR); Young Jo Lee, Seoul (KR)

(73) Assignee: SEEGENE, INC., Seoul (KR)

(*) Notice: Subject to any disclaimer, the term of this patent is extended or adjusted under 35 U.S.C. 154(b) by 191 days.

This patent is subject to a terminal disclaimer.

(21) Appl. No.: 15/124,700

(22) PCT Filed: Jun. 17, 2014

(86) PCT No.: PCT/KR2014/005309
§ 371 (c)(1),
(2) Date: Sep. 9, 2016

(87) PCT Pub. No.: WO2015/147377
PCT Pub. Date: Oct. 1, 2015

(65) Prior Publication Data
US 2017/0016049 A1 Jan. 19, 2017

Related U.S. Application Data

(60) Provisional application No. 61/979,545, filed on Apr. 15, 2014.

(30) Foreign Application Priority Data

Mar. 28, 2014 (KR) .................... 10-2014-0037310
May 9, 2014 (KR) ................ PCT/KR2014/004173

(51) Int. Cl.
*C12Q 1/68* (2018.01)
*G01N 25/04* (2006.01)
*C12Q 1/6816* (2018.01)
*C12Q 1/6827* (2018.01)
*C12Q 1/6858* (2018.01)

(52) U.S. Cl.
CPC ......... *C12Q 1/6816* (2013.01); *C12Q 1/6827* (2013.01); *C12Q 1/6858* (2013.01); *G01N 25/04* (2013.01)

(58) Field of Classification Search
CPC .............. C12Q 1/6816; C12Q 1/6827; C12Q 2527/107; C12Q 2561/101
See application file for complete search history.

(56) References Cited

U.S. PATENT DOCUMENTS

2005/0053950 A1 3/2005 Zudaire Ubani et al.
2012/0116686 A1 5/2012 Palais

FOREIGN PATENT DOCUMENTS

| WO | 2010013017 A1 | 2/2010 |
| WO | 2010017543 A1 | 2/2010 |
| WO | 2012048207 A2 | 4/2012 |
| WO | 2013115442 A1 | 8/2013 |
| WO | 2013133561 A1 | 9/2013 |
| WO | 2014022827 A1 | 2/2014 |

OTHER PUBLICATIONS

Chakravorty, S., et al.; Rapid Detection of Fluoroquinolone-Resistant and Heteroresistant Mycobacterium tuberculosis by Use of Sloppy Molecular Beacons and Dual Melting-Temperature Codes in a Real-Time PCR Assay; Journal of Clinical Microbiology, Mar. 2011, vol. 49, No. 3, pp. 932-940.
Liu, Q., et al.; Triplex real-time PCR melting curve analysis for detecting Mycobacterium tuberculosis mutations associated with resistance to second-line drugs in a single reaction; Journal of Antimicbrobial Chemotherapy, 2013, vol. 68, pp. 1097-1103.
Pierce, K., et al.; Rapid detection and identification of hepatitis C virus (HCV) sequences using mismatch-tolerant hyridization probes: A general method for analysis of sequence variation; Reports, 2013, vol. 55, No. 3, pp. 125-132.
Alvandi, E., et al.; Zip nucleic acid: a new reliable method to increase the melting temperature of real-time PCR probes; Journal of Diabetes & Metabolic Disorders, 2014, vol. 13, pp. 1-4.

*Primary Examiner* — David C Thomas
(74) *Attorney, Agent, or Firm* — Gianna Julian-Arnold; Saul Ewing Arnstein & Lehr LLP (57) ABSTRACT

The present invention relates to detection of a target nucleic acid sequence in a sample using two different detection temperatures. The present invention using difference between signals detected at two detection temperatures enables to decrease well-to-well variation or sample-to-sample variation generated in real-time PCR processes in more convenient and effective manner.

12 Claims, 4 Drawing Sheets

Specification includes a Sequence Listing.

Fig. 1A

Amplification Curves for Target [1]

[1] Target is a genomic DNA of *Ureaplasma parvum* (UP).
[2] Ratio represent the ratio of RFU at 60°C to RFU at 72°C in each of cycles.

Fig. 1B

|  | End-RFU[1] | | End-Ratio[2] |
|---|---|---|---|
|  | 72°C | 60°C |  |
| Average[3] | 4116 | 4770 | 0.063 |
| SD[4] | 384 | 442 | 0.003 |
| CV (%)[5] | 9.34 | 9.27 | 4.21 |

[1] End-RFU represents relative fluorescence units at 50th cycle.
[2] End-Ratio represents the Ratio of End-RFU at 60°C to End-RFU at 72°C.
[3] Average is obtained from End-RFUs or End-Ratios of ninety-six reactions.
[4] SD represents Standard Deviation
[5] CV (%) represents Coefficient of Variation (CV = SD ÷ Average x 100).

Fig. 2A

Amplification Curves for NTC[1]

[1] NTC represents No Target Control.
[2] Ratio represents the ratio of RFU at 60°C to RFU at 72°C in each of cycles.

Fig. 2B

| | Basal-RFU[1] | | Basal-Ratio[2] |
|---|---|---|---|
| | 72°C | 60°C | |
| Average[3] | 7585 | 7467 | 0.984 |
| SD[4] | 389 | 377 | 0.002 |
| CV (%)[5] | 5.13 | 5.05 | 0.23 |

[1] Basal-RFU represents the mean value of relative fluorescence units in all cycles
[2] Basal-Ratio represents the mean value of the Ratios in all cycles.
[3] Average is obtained from Basal-RFUs or Basal-Ratios of ninety-six reactions.
[4] SD represents Standard Deviation
[5] CV (%) represents Coefficient of Variation (CV = SD ÷ Average x 100).

SEQUENCE LISTING

```
<160> NUMBER OF SEQ ID NOS: 3

<210> SEQ ID NO 1
<211> LENGTH: 39
<212> TYPE: DNA
<213> ORGANISM: Artificial Sequence
<220> FEATURE:
<223> OTHER INFORMATION: UP-F
<220> FEATURE:
<221> NAME/KEY: misc_feature
<222> LOCATION: (25)..(29)
<223> OTHER INFORMATION: n denotes deoxyinosine

<400> SEQUENCE: 1
gcacaatttg gatcattaaa aggtnnnnnt gaattcagt                          39

<210> SEQ ID NO 2
<211> LENGTH: 39
<212> TYPE: DNA
<213> ORGANISM: Artificial Sequence
<220> FEATURE:
<223> OTHER INFORMATION: UP-R
<220> FEATURE:
<221> NAME/KEY: misc_feature
<222> LOCATION: (25)..(29)
<223> OTHER INFORMATION: n denotes deoxyinosine

<400> SEQUENCE: 2
ggttctcaag caacaatatc agctnnnnna ccaacttct                          39

<210> SEQ ID NO 3
<211> LENGTH: 25
<212> TYPE: DNA
<213> ORGANISM: Artificial Sequence
<220> FEATURE:
<223> OTHER INFORMATION: UP-P

<400> SEQUENCE: 3
cccagctatt gcacatggtg ttgat                                         25
```

DETECTION OF A TARGET NUCLEIC ACID SEQUENCE USING TWO DIFFERENT DETECTION TEMPERATURES

CROSS REFERENCE TO RELATED APPLICATIONS

This application claims the priority of PCT/KR2014/005309, filed on Jun. 17, 2014, which claims priority to PCT/KR2014/004173, filed on May 9, 2014, which claims priority to U.S. Provisional Patent Application No. 61/979,545, filed on Apr. 15, 2014, which claims priority to Korean Patent Application No. 10-2014-0037310, filed Mar. 28, 2014, the entire contents of each of which are hereby incorporated in total by reference.

SEQUENCE LISTING

This application incorporates by reference the Sequence Listing contained in an ASCII text file named "361406_00032_SeqList.txt" submitted via EFS-Web. The text file was created on Aug. 31, 2016, and is 2 kb in size.

BACKGROUND OF THE INVENTION

Field of the Invention

The present invention relates to detection of a target nucleic acid sequence in a sample using two different detection temperatures.

Description of the Related Art

For detection of target nucleic acid sequences, real-time detection methods are widely used to detect target nucleic acid sequences with monitoring target amplification in a real-time manner. The real-time detection methods generally use labeled probes or primers specifically hybridized with target nucleic acid sequences. The exemplified methods by use of hybridization between labeled probes and target nucleic acid sequences include Molecular beacon method using dual-labeled probes with hairpin structure (Tyagi et al, Nature Biotechnology v. 14 Mar. 1996), HyBeacon method (French D J et al., Mol. Cell Probes, 15(6):363-374 (2001)), Hybridization probe method using two probes labeled each of donor and acceptor (Bernad et al, 147-148 Clin Chem 2000; 46) and Lux method using single-labeled oligonucleotides (U.S. Pat. No. 7,537,886). TaqMan method (U.S. Pat. Nos. 5,210,015 and 5,538,848) using dual-labeled probes and its cleavage by 5'-nuclease activity of DNA polymerase is also widely employed in the art.

The exemplified methods using labeled primers include Sunrise primer method (Nazarenko et al, 2516-2521 Nucleic Acids Research, 1997, v. 25 no. 12, and U.S. Pat. No. 6,117,635), Scorpion primer method (Whitcombe et al, 804-807, Nature Biotechnology v. 17 Aug. 1999 and U.S. Pat. No. 6,326,145) and TSG primer method (WO 2011/078441).

As alternative approaches, real-time detection methods using duplexes formed depending on the presence of target nucleic acid sequences have been proposed: Invader assay (U.S. Pat. Nos. 5,691,142, 6,358,691 and 6,194,149), PTOCE (PTO cleavage AND extension) method (WO 2012/096523), PCE-SH (PTO Cleavage and Extension-Dependent Signaling Oligonucleotide Hybridization) method (WO 2013/115442), PCE-NH (PTO Cleavage and Extension-Dependent Non-Hybridization) method (PCT/KR2013/012312).

The real-time detection technologies conventionally detect signals generated from fluorescent labels at a single detection temperature with or with no target amplification.

In the real-time detection method, it is very likely to detect signals with variations owing to internal and external conditions for amplification and detection including minor variations in reaction components or thermal cycling conditions, small well-to-well temperature variations, deficiencies in the signal uniformity due to the instrument optical system, multiple complex optical pathways, and human error such as aliquoting errors during preparing reaction mixtures. To reduce or remove the signal variations, use of reference dye or a suitable control, improvement of instrument and use of master mix have been proposed. Unfortunately, such approaches have shown limitations in solving the problems associated with signal variations.

Accordingly, there is a long-felt need in the art to solve the problems associated with signal variations in more fundamental and convenient manner.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to develop novel methods for detecting a target nucleic acid sequence with reducing or removing influences from conditions for reactions and/or detection that cause signal variations. As a result, we have found that detections at two different detection temperatures for a target nucleic acid sequence can reduce influences from conditions causing signal variations, such that more reliable results for determining the presence of a target nucleic acid sequence can be produced.

The effects of decreasing signal variations are ascribed to the unique approach to detect a single target nucleic acid sequence using two detection temperatures and the unique approach gives a multitude of advantages as well as decrease in signal variations.

Accordingly, it is an object of this invention to provide a method for detecting a target nucleic acid sequence in a sample using two different detection temperatures.

It is another object of this invention to provide a computer readable storage medium containing instructions to configure a processor to perform a method for determining the presence of a target nucleic acid sequence in a sample using two different detection temperatures.

It is still another object of this invention to provide a device for detecting a target nucleic acid sequence in a sample using two different detection temperatures.

Other objects and advantages of the present invention will become apparent from the detailed description to follow taken in conjugation with the appended claims and drawings.

DETAILED DESCRIPTION OF THIS INVENTION

Conventional methods generally utilize a single detection temperature for detection of a target nucleic acid sequence. For instance, in conventional real-time detection methods accompanied by nucleic acid amplification reaction such as PCR, signals are collected at each cycle and at a certain temperature and then the presence or the quantity of a target nucleic acid sequence is determined by using the collected signals. Alternatively, following amplification reactions, a target nucleic acid sequence may be qualified or quantified by using signal detected at a certain temperature.

Contrary to common knowledge of those skilled in the art that two detection temperatures are not required, the present invention employs two different detection temperatures for detection of a target nucleic acid sequence. For example, in a real-time detection method accompanied by nucleic acid amplification reaction such as PCR, the present invention collects signals at two detection temperatures at each cycle and then determines the presence of and measures the quantity of a target nucleic acid sequence using the collected signals. Alternatively, following amplification reactions, the present invention may qualify or quantify a target nucleic acid sequence by using signals detected at two detection temperatures.

The most prominent feature of the present invention is to use two detection temperatures and furthermore adapt a difference between signals at the two detection temperatures to detection of a single target nucleic acid sequence. The present invention provides a novel signal form reflecting such difference between signals at the two detection temperatures and qualifies and quantifies a target nucleic acid sequence by using the novel signal form.

The present invention can offer a multitude of advantages over conventional technologies using a single detection temperature.

Where several samples whose each contains an identical target nucleic acid sequence are prepared and used for detection, there may be difference of detection results from each other in reaction vessels. Such difference may be owing to differences of reaction conditions between reaction vessels. Furthermore, where different detection devices are used, such difference of detection results may be more severe due to differences of components or setting in the devices. The difference becomes more considerable factor when the amount of target nucleic acid sequences becomes smaller or results obtained from repetitive experiments are compared. To decrease deviations in samples between vessels or detection apparatuses, conventional technologies are seeking solutions in view of software or hardware or using a signal from an additional control.

The present invention detects signals at two detection temperatures for a single target nucleic acid sequence in a reaction vessel. The present invention permits to yield detection results under substantially identical reaction conditions except for detection temperatures. The present invention permits to provide results being free from influences of reaction conditions by suitably processing detection results obtained at two different detection temperatures, which is employed to determine the presence of a target nucleic acid sequence.

Detecting a target nucleic acid sequence by using two different detection temperatures enables to decrease signal variations caused by influence of reaction conditions. The decrease in signal variations is very crucial in determining the presence or quantity of a target nucleic acid sequence in more accurate and reliable manner.

The elements of the present invention are selected in compliance with the feature of the present invention and fabricated into the interesting surprising process of the present invention for detect a target nucleic acid sequence.

In one aspect of this invention, there is provided a method for detecting a target nucleic acid sequence in a sample using two different detection temperatures, comprising:

(a) incubating a reaction mixture containing the sample and a signal-generating means for detection of the target nucleic acid sequence in a reaction vessel and detecting signals generated at a relatively high detection temperature and at a relatively low detection temperature; and (b) determining the presence of the target nucleic acid sequence by a processed signal obtained from a difference between the signal detected at the relatively high detection temperature and the signal detected at the relatively low detection temperature.

The present invention will be described in more detail as follows:

Step (a): Incubation with Signal-Generating Means and Signal Detection

Firstly, the reaction mixture containing the sample to be analyzed is incubated with a signal-generating means for detection of the target nucleic acid sequence in a reaction vessel and then generated signals are detected.

The present invention utilizes a signal-generating mean for generating signal for the target nucleic acid sequence. The term used herein "signal-generating means" refers to any material used in generation of signals indicating the presence of the target nucleic acid sequence, for example including oligonucleotides, labels and enzymes. Alternatively, the term used herein "signal-generating means" can be used to refer to any methods using the materials for signal generation.

According to an embodiment of this invention, the incubation is preformed in the conditions allowing for a signal generation by the signal-generation means. Such conditions include temperatures, salt concentrations and pH of solutions.

Examples of the oligonucleotides serving as signal-generating means include: oligonucleotides to be specifically hybridized with target nucleic acid sequences (e.g., probes and primers); where oligonucleotides hybridized with target nucleic acid sequences are cleaved to release a fragment, capture oligonucleotides to be specifically hybridized with the fragment; where the fragment hybridized with the capture oligonucleotide is extended to form an extended strand, oligonucleotides to be specifically hybridized with the extended strand; oligonucleotides to be specifically hybridized with the capture oligonucleotide; and combinations thereof.

The label may be linked to oligonucleotides or may be in the free form. The label may be incorporated into extended products during an extension reaction.

Where the cleavage of oligonucleotides is used in signal generation, examples of the enzyme include 5'-nuclease and 3'-nuclease, particularly nucleic acid polymerase having 5'-nuclease activity, nucleic acid polymerase having 3'-nuclease activity or FEN nuclease.

In the present invention, signals may be generated by using various materials described above in various fashions.

According to an embodiment, the signal-generating means is a signal-generating means to generate a signal in a dependent manner on the formation of a duplex.

According to an embodiment, the duplex includes a double stranded target nucleic acid sequence.

The expression used herein "generate a signal in a dependent manner on the formation of a duplex" in conjunction with signal-generating means refers to that signal to be detected is provided being dependent on association or dissociation of two nucleic acid molecules. The expression includes that signal is provided by a duplex formed being dependent on the presence of a target nucleic acid sequence. In addition, the expression includes that signal is provided by inhibition of hybridization of a duplex. The expression is different from providing a signal by cleavage.

Particularly, the signal is generated by the formation of a duplex between a target nucleic acid sequence and a detection oligonucleotide specifically hybridized with the target nucleic acid sequence.

The term used herein "detection oligonucleotide" is an oligonucleotide which is involved in generation of signal to be detected. According to an embodiment of the present invention, the detection oligonucleotide includes an oligonucleotide which is specifically hybridized with a target nucleic acid sequence and is involved in an actual signal generation. For example, the hybridization or non-hybridization of a detection oligonucleotide to the target nucleic acid determines the signal generation.

The signal by the formation of a duplex between a target nucleic acid sequence and the detection oligonucleotide may be generated by various methods, including Scorpion method (Whitcombe et al, Nature Biotechnology 17:804-807 (1999)), Sunrise (or Amplifluor) method (Nazarenko et al, Nucleic Acids Research, 25(12):2516-2521 (1997), and U.S. Pat. No. 6,117,635), Lux method (U.S. Pat. No. 7,537, 886), Plexor method (Sherrill C B, et al., Journal of the American Chemical Society, 126:4550-45569 (2004)), Molecular Beacon method (Tyagi et al, Nature Biotechnology v. 14 Mar. 1996), HyBeacon method (French D J et al., Mol. Cell Probes, 15(6):363-374 (2001)), adjacent hybridization probe method (Bernard, P. S. et al., Anal. Biochem., 273:221 (1999)) and LNA method (U.S. Pat. No. 6,977, 295). Particularly, the signal is generated by a duplex formed in a dependent manner on cleavage of a mediation oligonucleotide specifically hybridized with the target nucleic acid sequence.

The term used herein "mediation oligonucleotide" is an oligonucleotide which mediates production of a duplex not containing a target nucleic acid sequence.

According to an embodiment of the present invention, the cleavage of the mediation oligonucleotide per se does not generate signal and a fragment formed by the cleavage is involved in successive reactions for signal generation following hybridization and cleavage of the mediation oligonucleotide.

According to an embodiment, the hybridization or cleavage of the mediation oligonucleotide per se does not generate signal.

According to an embodiment of the present invention, the mediation oligonucleotide includes an oligonucleotide which is hybridized with a target nucleic acid sequence and cleaved to release a fragment, leading to mediate the production of a duplex.

The signal by the duplex formed in a dependent manner on cleavage of the mediation oligonucleotide may be generated by various methods, including PTOCE (PTO cleavage and extension) method (WO 2012/096523), PCE-SH (PTO Cleavage and Extension-Dependent Signaling Oligonucleotide Hybridization) method (WO 2013/115442) and PCE-NH (PTO Cleavage and Extension-Dependent Non-Hybridization) method (PCT/KR2013/012312).

The signal by the duplex formed in a dependent manner on cleavage of the mediation oligonucleotide includes the signal provided by inhibition of the formation of other duplex by the duplex formed in a dependent manner on cleavage of the mediation oligonucleotide (e.g. PCE-NH).

For example, where the signal by the duplex formed in a dependent manner on cleavage of the mediation oligonucleotide is generated by PTOCE method, the signal-generating means comprises an upstream oligonucleotide and a PTO (Probing and Tagging Oligonucleotide) having a hybridizing nucleotide sequence complementary to the target nucleic acid sequence, a CTO (Capturing and Templating Oligonucleotide), suitable label and a template-dependent nucleic acid polymerase having 5' nuclease activity. The PTO comprises (i) a 3'-targeting portion comprising a hybridizing nucleotide sequence complementary to the target nucleic acid sequence and (ii) a 5'-tagging portion comprising a nucleotide sequence non-complementary to the target nucleic acid sequence. The CTO comprises in a 3' to 5' direction (i) a capturing portion comprising a nucleotide sequence 'complementary to the 5'-tagging portion or a part of the 5'-tagging portion of the PTO and (ii) a templating portion comprising a nucleotide sequence non-complementary to the 5'-tagging portion and the 3'-targeting portion of the PTO.

The particular example of the signal generation by PTOCE method comprises the steps of:

(a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; and (d) performing an extension reaction using the resultant of the step (c) and a template-dependent nucleic acid polymerase; wherein the fragment hybridized with the capturing portion of the CTO is extended and an extended duplex is formed; wherein the extended duplex has a $T_m$ value adjustable by (i) a sequence and/or length of the fragment, (ii) a sequence and/or length of the CTO or (iii) the sequence and/or length of the fragment and the sequence and/or length of the CTO; wherein the extended duplex provides a target signal by (i) at least one label linked to the fragment and/or the CTO, (ii) a label incorporated into the extended duplex during the extension reaction, (iii) a label incorporated into the extended duplex during the extension reaction and a label linked to the fragment and/or the CTO, or (iv) an intercalating label; and (e) detecting the extended duplex by measuring the target signal at a predetermined temperature that the extended duplex maintains its double-stranded form, whereby the presence of the extended duplex indicates the presence of the target nucleic acid sequence. In this case, the method further comprises repeating all or some of the steps (a)-(e) with denaturation between repeating cycles.

In the phrase "denaturation between repeating cycles", the term "denaturation" means to separate a double-stranded nucleic acid molecule to a single-stranded nucleic acid molecule.

In the step (a) of PTOCE method, a primer set for amplification of the target nucleic acid sequence may be used instead of the upstream oligonucleotide. In this case, the method further comprises repeating all or some of the steps (a)-(e) with denaturation between repeating cycles.

The PTOCE method can be classified as a process in which the PTO fragment hybridized with the CTO is extended to form an extended strand and the extended strand is then detected. The PTOCE method is characterized that the formation of the extended strand is detected by using the duplex between the extended strand and the CTO.

There is another approach to detect the formation of the extended strand. For example, the formation of the extended strand may be detected by using an oligonucleotide specifically hybridized with the extended strand (e.g., PCE-SH method). In this method, the signal may be provided from (i) a label linked to the oligonucleotide specifically hybridized with the extended strand, (ii) a label linked to the oligonucleotide specifically hybridized with the extended strand and a label linked to the PTO fragment, (iii) a label linked to the oligonucleotide specifically hybridized with the extended strand and a label incorporated into the extended strand during the extension reaction, or (iv) a label linked to the oligonucleotide specifically hybridized with the extended strand and an intercalating dye. Alternatively, the signal may be provided from (i) a label linked to the extended strand or (ii) an intercalating dye.

Alternatively, the detection of the formation of the extended strand is performed by another method in which inhibition of the hybridization between the CTO and an oligonucleotide being specifically hybridizable with the CTO is detected (e.g. PCE-NH method). Such inhibition is considered to be indicative of the presence of a target nucleic acid sequence. The signal may be provided from (i) a label linked to the oligonucleotide being hybridizable with the CTO, (ii) a label linked to the CTO, (iii) a label linked to the oligonucleotide being hybridizable with the CTO and a label linked to the CTO, or (iv) an intercalating label.

According to an embodiment, the oligonucleotide being specifically hybridizable with the CTO has an overlapping sequence with the PTO fragment.

According to an embodiment, the detection oligonucleotide includes the oligonucleotide being specifically hybridizable with the extended strand (e.g., PCE-SH method) and oligonucleotide being specifically hybridizable with the CTO (e.g. PCE-NH method). According to an embodiment, the detection oligonucleotide includes the extended strand produced during a reaction or CTO.

The PTOCE-based methods commonly involve the formation of the extended strand depending on the presence of a target nucleic acid sequence. The term "PTOCE-based method" is used herein to intend to encompass various methods for providing signals comprising the formation of an extended strand through cleavage and extension of PTO.

The example of signal generation by the PTOCE-based methods comprises the steps of: (a) hybridizing the target nucleic acid sequence with the upstream oligonucleotide and the PTO; (b) contacting the resultant of the step (a) to an enzyme having a 5' nuclease activity under conditions for cleavage of the PTO; wherein the upstream oligonucleotide or its extended strand induces cleavage of the PTO by the enzyme having the 5' nuclease activity such that the cleavage releases a fragment comprising the 5'-tagging portion or a part of the 5'-tagging portion of the PTO; (c) hybridizing the fragment released from the PTO with the CTO; wherein the fragment released from the PTO is hybridized with the capturing portion of the CTO; (d) performing an extension reaction using the resultant of the step (c) and a template-dependent nucleic acid polymerase; wherein the fragment hybridized with the capturing portion of the CTO is extended to form an extended strand; and (e) detecting the formation of the extended strand by detecting signal generated dependent on the presence of the extended strand. In the step (a), a primer set for amplification of the target nucleic acid sequence may be used instead of the upstream oligonucleotide. In this case, the method further comprises repeating all or some of the steps (a)-(e) with denaturation between repeating cycles.

According to an embodiment, the signal generated by the formation of a duplex includes signals induced by hybridization of the duplex (e.g., hybridization of the duplex per se, or hybridization of a third oligonucleotide) or by inhibition of hybridization of a third oligonucleotide due to the formation of a duplex.

According to an embodiment, the signal-generating means is a signal-generating means to generate a signal in a dependent manner on cleavage of a detection oligonucleotide.

Particularly, the signal is generated by hybridization of the detection oligonucleotide with a target nucleic acid sequence and then cleavage of the detection oligonucleotide.

The signal by hybridization of the detection oligonucleotide with a target nucleic acid sequence and then cleavage of the detection oligonucleotide may be generated by various methods, including TaqMan probe method (U.S. Pat. No. 5,210,015).

Where the signal is generated by TaqMan probe method, the signal-generating means includes a primer set for amplification of a target nucleic acid sequence, TaqMan probe having a suitable label (e.g., interactive dual label) and nucleic acid polymerase having 5'-nuclease activity. The TaqMan probe hybridized with a target nucleic acid sequence is cleaved during target amplification and generates signal indicating the presence of the target nucleic acid sequence.

The particular example generating signal by TaqMan probe method comprises the step of: (a) hybridizing the primer set and TaqMan probe having a suitable label (e.g., interactive dual label) with the target nucleic acid sequence; (b) amplifying the target nucleic acid sequence by using the resultant of the step (a) and nucleic acid polymerase having 5'-nuclease activity, wherein the TaqMan probe is cleaved to release the label; and (c) detecting a signal generation from the released label.

Particularly, the signal is generated by cleavage of the detection oligonucleotide in a dependent manner on cleavage of a mediation oligonucleotide specifically hybridized with the target nucleic acid sequence.

The signal by cleavage of the detection oligonucleotide in a dependent manner on cleavage of the mediation oligonucleotide may be generated by various methods, including Invader assay (U.S. Pat. No. 5,691,142), PCEC (PTO Cleavage and Extension-Dependent Cleavage) method (WO 2012/134195) and a method described in U.S. Pat. No. 7,309,573. In particular, the method described in U.S. Pat. No. 7,309,573 may be considered as one of PTOCE-based methods using signal generation by cleavage, and in the method, the formation of the extended strand may be detected by detecting cleavage of an oligonucleotide specifically hybridized with the CTO by the formation of the extended strand. Invader assay forms a fragment by cleavage of a mediation oligonucleotide and induces successive cleavage reactions with no extension of the fragment.

According to an embodiment of this invention, the step (a) is performed in a signal amplification process concomitantly with a nucleic acid amplification.

In the present invention, the signal generated by signal-generating means may be amplified simultaneously with target amplification. Alternatively, the signal may be amplified with no target amplification.

According to an embodiment of this invention, the signal generation is performed in a process involving signal amplification together with target amplification.

According to an embodiment of this invention, the target amplification is performed in accordance with PCR (polymerase chain reaction). PCR is widely employed for target amplification in the art, including cycles of denaturation of a target sequence, annealing (hybridization) between the target sequence and primers and primer extension (Mullis et al. U.S. Pat. Nos. 4,683,195, 4,683,202 and 4,800,159; Saiki et al., (1985) Science 230, 1350-1354). The signal may be amplified by applying the signal generation methods described above (e.g., TaqMan method and PTOCE-based methods) to the PCR process. According to an embodiment, the present invention provides signals by real-time PCR method. According to an embodiment, the amplification of the target nucleic acid sequence is performed by PCR (polymerase chain reaction), LCR (ligase chain reaction, see. Wiedmann M, et al., "Ligase chain reaction (LCR)—overview and applications." PCR Methods and Applications 1994 February; 3(4):S51-64), GLCR (gap filling LCR, see WO 90/01069, EP 439182 and WO 93/00447), Q-beta (Q-beta replicase amplification, see Cahill P, et al., Clin Chem., 37(9):1482-5 (1991), U.S. Pat. No. 5,556,751), SDA (strand displacement amplification, see G T Walker et al., Nucleic Acids Res. 20(7):16911696 (1992), EP 497272), NASBA (nucleic acid sequence-based amplification, see Compton, 3. Nature 350(6313):912 (1991)), TMA (Transcription-Mediated Amplification, see Hofmann W P et al., 3 Clin Virol. 32(4):289-93 (2005); U.S. Pat. No. 5,888,779) .) or RCA (Rolling Circle Amplification, see Hutchison C. A. et al., Proc. Natl Acad. Sci. USA. 102:1733217336 (2005)).

The amplification methods described above may amplify target sequences through repeating a series of reactions with or without changing temperatures. The unit of amplification comprising the repetition of a series of reactions is expressed as a "cycle". The unit of cycles may be expressed as the number of the repetition or time being dependent on amplification methods.

For example, the detection of signals may be performed at each cycle of amplification, selected several cycles or end-point of reactions. According to an embodiment, where signals are detected at at least two cycles, the detection of signal in an individual cycle may be performed at all detection temperatures or some selected detection temperatures. According to an embodiment of this invention, the detection is performed at the relatively high detection temperature in odd numbered cycles and at the relatively high detection temperature in even numbered cycles.

According to an embodiment of this invention, the incubation is preformed under conditions allowing for target amplification as well as signal generation by the signal-generation means.

According to an embodiment of this invention, the step (a) is performed in a signal amplification process without a nucleic acid amplification.

Where the signal is generated by methods including cleavage of an oligonucleotide, the signal may be amplified with no target amplification. For example, the step (a) may be performed with amplification of signals but with no amplification of target sequences in accordance with CPT method (Duck P, et al., Biotechniques, 9:142-148 (1990)), Invader assay (U.S. Pat. Nos. 6,358,691 and 6,194,149), PTOCE-based methods (e.g., PCE-SH method, PCE-NH method and PCEC method) or CER method (WO 2011/037306).

The signal amplification methods described above may amplify signals through repeating a series of reactions with or without changing temperatures. The unit of signal amplification comprising the repetition of a series of reactions is expressed as a "cycle". The unit of cycles may be expressed as the number of the repetition or time being dependent on amplification methods.

For example, the generation and detection of signals may be performed at each cycle of amplification, selected several cycles or end-point of reactions.

The label useful in the present invention includes various labels known in the art. For example, the label useful in the present invention includes a single label, an interactive dual label, an intercalating dye and an incorporating label.

The single label includes, for example, a fluorescent label, a luminescent label, a chemiluminescent label, an electrochemical label and a metal label. According to an embodiment, the single label provides a different signal (e.g., different signal intensities) depending on its presence on a double strand or single strand. According to an embodiment, the single label is a fluorescent label. The preferable types and binding sites of single fluorescent labels used in this invention are disclosed U.S. Pat. Nos. 7,537,886 and 7,348, 141, the teachings of which are incorporated herein by reference in their entity. For example, the single fluorescent label includes JOE, FAM, TAMRA, ROX and fluorescein-based label. The single label may be linked to oligonucleotides by various methods. For instance, the label is linked to probes through a spacer containing carbon atoms (e.g., 3-carbon spacer, 6-carbon spacer or 12-carbon spacer).

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent. In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent. The interactive label system includes a dual label based on "on contact-mediated quenching" (Salvatore et al., Nucleic Acids Research, 2002 (30) no. 21 e122 and Johansson et al., J. AM. CHEM. SOC 2002 (124) pp 6950-6956). The interactive label system includes any label system in which signal change is induced by interaction between at least two molecules (e.g. dye).

The reporter molecule and the quencher molecule useful in the present invention may include any molecules known in the art. Examples of those are: Cy2™ (506), YO-PRO™-1 (509), YOYO™-1 (509), Calcein (517), FITC (518), FluorX™ (519), Alexa™ (520), Rhodamine 110 (520), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DiIC (5) (665), Cy5™ (670), Thiadicarbocyanine (671), Cy5.5 (694), HEX (556), TET (536), Biosearch Blue (447), CAL Fluor Gold 540 (544), CAL Fluor Orange 560 (559), CAL Fluor Red 590 (591), CAL Fluor Red 610 (610), CAL Fluor Red 635 (637), FAM (520), Fluorescein (520), Fluorescein-C3 (520), Pulsar 650 (566), Quasar 570 (667), Quasar 670 (705) and Quasar 705 (610). The numeric in parenthesis is a maximum emission wavelength in nanometer. Preferably, the reporter molecule and the quencher molecule include JOE, FAM, TAMRA, ROX and fluorescein-based label.

Suitable fluorescence molecule and suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, 2$^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, 6$^{th}$ Edition (Molecular Probes, Eugene, Oreg., 1996) U.S. Pat. Nos. 3,996,345 and 4,351,760.

It is noteworthy that a non-fluorescent quencher molecule (e.g. black quencher or dark quencher) capable of quenching a fluorescence of a wide range of wavelengths or a specific wavelength may be used in the present invention.

In the signaling system comprising the reporter and quencher molecules, the reporter encompasses a donor of FRET and the quencher encompasses the other partner (acceptor) of FRET. For example, a fluorescein dye is used as the reporter and a rhodamine dye as the quencher.

The interactive dual label may be linked to one strand of a duplex. Where the strand containing the interactive dual label leaves in a single stranded state, it forms a hairpin or random coil structure to induce quenching between the interactive dual label. Where the strand forms a duplex, the quenching is relieved. Alternatively, where the interactive dual label is linked to nucleotides adjacently positioned on the strand, the quenching between the interactive dual label occurs. Where the strand forms a duplex and then is cleaved, the quenching becomes relieved.

Each of the interactive dual label may be linked to each of two strands of the duplex. The formation of the duplex induces quenching and denaturation of the duplex induces unquenching. Alternatively, where one of the two stands is cleaved, the unquenching may be induced.

Exemplified intercalating dyes useful in this invention include SYBR™ Green I, PO-PRO™-1, BO-PRO™-1, SYTO™43, SYTO™44, SYTO™45, SYTOX™ Blue, POPO™-1, POPO™-3, BOBO™-1, BOBO™-3, LO-PRO™-1, JO-PRO™-1, YO—PRO™1, TO-PRO™1, SYTO™11, SYTO™13, SYTO™15, SYTO™16, SYTO™20, SYTO™23, TOTO™-3, YOYO™3, GelStar™ and thiazole orange. The intercalating dyes intercalate specifically into double-stranded nucleic acid molecules to generate signals.

The incorporating label may be used in a process to generate signals by incorporating a label during primer extension (e.g., Plexor method, Sherrill C B, et al., Journal of the American Chemical Society, 126:4550-45569 (2004)). The incorporating label may be also used in a signal generation by a duplex formed in a dependent manner on cleavage of a mediation oligonucleotide hybridized with the target nucleic acid sequence.

The incorporating label may be generally linked to nucleotides. The nucleotide having a non-natural base may be also used.

The term used herein "non-natural base" refers to derivatives of natural bases such as adenine (A), guanine (G), thymine (T), cytosine (C) and uracil (U), which are capable of forming hydrogen-bonding base pairs. The term used herein "non-natural base" includes bases having different base pairing patterns from natural bases as mother compounds, as described, for example, in U.S. Pat. Nos. 5,432,272, 5,965,364, 6,001,983, and 6,037,120. The base pairing between non-natural bases involves two or three hydrogen bonds as natural bases. The base pairing between non-natural bases is also formed in a specific manner. Specific examples of non-natural bases include the following bases in base pair combinations: iso-C/iso-G, iso-dC/iso-dG, K/X, H/J, and M/N (see U.S. Pat. No. 7,422,850).

Where the signal is generated by the PTOCE method, a nucleotide incorporated during the extension reaction may have a first non-natural base and the CTO may have a nucleotide having a second non-natural base with a specific binding affinity to the first non-natural base.

The term used herein "target nucleic acid", "target nucleic acid sequence" or "target sequence" refers to a nucleic acid sequence of interest for qualification or quantification. The target nucleic acid sequence comprises a sequence in a single strand as well as in a double strand. The target nucleic acid sequence comprises a sequence initially present in a nucleic acid sample as well as a sequence newly generated in reactions.

The target nucleic acid sequence may include any DNA (gDNA and cDNA), RNA molecules their hybrids (chimera nucleic acid). The sequence may be in either a double-stranded or single-stranded form. Where the nucleic acid as starting material is double-stranded, it is preferred to render the two strands into a single-stranded or partially single-stranded form. Methods known to separate strands includes, but not limited to, heating, alkali, formamide, urea and glycoxal treatment, enzymatic methods (e.g., helicase action), and binding proteins. For instance, strand separation can be achieved by heating at temperature ranging from 80° C. to 105° C. General methods for accomplishing this treatment are provided by Joseph Sambrook, et al., *Molecu-* lar *Cloning, A Laboratory Manual*, Cold Spring Harbor Laboratory Press, Cold Spring Harbor, N.Y. (2001).

Where a mRNA is employed as starting material, a reverse transcription step is necessary prior to performing annealing step, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., Nucleic Acids Res. 16:10366 (1988)). For reverse transcription, an oligonucleotide dT primer hybridizable to poly A tail of mRNA, random primers or target-specific primers may be used.

The target nucleic acid sequence includes any naturally occurring prokaryotic, eukaryotic (for example, protozoans and parasites, fungi, yeast, higher plants, lower and higher animals, including mammals and humans), viral (for example, Herpes viruses, HIV, influenza virus, Epstein-Barr virus, hepatitis virus, polio virus, etc.), or viroid nucleic acid. The nucleic acid molecule can also be any nucleic acid molecule which has been or can be recombinantly produced or chemically synthesized. Thus, the nucleic acid sequence may or may not be found in nature. The target nucleic acid sequence may include known or unknown sequences.

The term used herein "sample" refers to any cell, tissue, or fluid from a biological source, or any other medium that can advantageously be evaluated according to this invention, including virus, bacteria, tissue, cell, blood, serum, plasma, lymph, milk, urine, faeces, ocular fluid, saliva, semen, brain extracts, spinal cord fluid (SCF), appendix, spleen and tonsillar tissue extracts, amniotic fluid, ascitic fluid and non-biological samples (e.g., food and water). In addition, the sample includes natural-occurring nucleic acid molecules isolated from biological sources and synthetic nucleic acid molecules.

The amplification of the target nucleic acid sequence is accomplished by target amplification means including a primer set for amplification and nucleic acid polymerase.

The nucleic acid polymerase useful in the present invention is a thermostable DNA polymerase obtained from a variety of bacterial species, including *Thermus aquaticus* (Taq), *Thermus thermophilus* (Tth), *Thermus filiformis, Thermis flavus, Thermococcus literalis, Thermus antranikianii, Thermus caldophilus, Thermus chliarophilus, Thermus flavus, Thermus igniterrae, Thermus lacteus, Thermus oshimai, Thermus ruber, Thermus rubens, Thermus scotoductus, Thermus silvanus, Thermus* species Z05, *Thermus* species sps 17, *Thermus thermophilus, Thermotoga maritima, Thermotoga neapolitana, Thermosipho africanus, Thermococcus litoralis, Thermococcus barossi, Thermococcus gorgonarius, Thermotoga maritima, Thermotoga neapolitana, Thermosipho africanus, Pyrococcus woesei, Pyrococcus horikoshii, Pyrococcus abyssi, Pyrodicbum occultum, Aquifex pyrophllus* and *Aquifex aeolieus*. Particularly, the thermostable DNA polymerase is Taq polymerase.

According to an embodiment of the present invention, the amplification of the target nucleic acid sequence is accomplished by an asymmetric PCR. The ratio of primers may be selected in consideration of cleavage or hybridization of downstream oligonucleotides.

During or after the incubation (reaction) of the reaction mixture containing the sample with the signal-generating means to generate signal, the generated signals are detected by using a detector.

The most prominent features of the present invention is to determine the presence of the target nucleic acid sequence by detecting signals at two different detection temperatures and using the difference between signals detected at the temperatures.

The present invention uses that there are temperatures to allow signal generation in a dependent manner on signal-generating means. For example, when a signal-generating means generates a signal upon hybridization (or association) between two nucleic acid molecules and do not generate a signal upon non-hybridization (or dissociation) between them, a signal is generated at temperatures allowing hybridization between two nucleic acid molecules, however, no signal is generated at temperatures failing to hybridize between two nucleic acid molecules. The temperatures are affected by the $T_m$ value of the hybrid of the two nucleic acid molecules employed in the signal-generation means.

Where the signal generation method using a released fragment with a label after cleavage is employed, the signal may be theoretically detected at any temperature (e.g., 25-99° C.).

Temperature ranges to generate signals indicating the presence of a target nucleic acid sequence may be different depending on signal-generating means, which should be considered in selecting the two detection temperatures.

Generally, the relatively high detection temperature and the relatively low detection temperature may be selected within a temperature range capable of generating a signal by signal-generating means to indicate a target nucleic acid sequence when the target nucleic acid sequence is present.

Alternatively, the relatively high detection temperature may be selected within a temperature range not to generate a signal by signal-generating means to indicate a target nucleic acid sequence even when the target nucleic acid sequence is present, and the relatively low detection temperature may be selected within a temperature range to generate signal by signal-generating means to indicate a target nucleic acid sequence when the target nucleic acid sequence is present.

According to an embodiment, the detection temperatures for a target nucleic acid sequence are selected in considering temperatures to permit difference in signals at the relatively high detection temperature and at the relatively low detection temperature.

According to the present invention, when signals indicating the presence of a target nucleic acid sequence are detected in a reaction vessel at predetermined two detection temperatures, there is a signal change between the signals. For example, where a fluorescent signal is used, a fluorescent intensity detected at one of the two detection temperatures may be different from that detected at the other detection temperature. The causes for such signal change may include alternation of temperature-dependent photoemission characteristics of labels, change in the number of duplexes responsible for signal generation and conformational change of labeled oligonucleotides.

Moreover, there may be the signal change in a certain pattern (or rule). For instance, such signal change exhibits within certain range, at less than or more than certain level.

According to an embodiment, the relatively high detection temperature and the relatively low detection temperature are selected within a temperature range to generate signal by signal-generating means to indicate a target nucleic acid sequence when the target nucleic acid sequence is present, and the detection temperatures for a target nucleic acid sequence are selected in considering temperatures to permit difference in signals at the relatively high detection temperature and at the relatively low detection temperature.

According to an embodiment, the relatively high detection temperature and the relatively low detection temperature at which the detection are carried out may be predetermined. For example, the relatively high detection temperature and the relatively low detection temperature are predetermined as 72° C. and 60° C., respectively, and then signal-generating means suitable for the detection temperatures is constructed, followed by performing the step (a).

According to an embodiment, the signal-generating mean for the target nucleic acid sequence is firstly constructed and then detection temperatures for the target nucleic acid sequence are allocated, followed by performing the step (a).

According to an embodiment of this invention, when the signal-generating means generates a signal in a dependent manner on the formation of a duplex, the detection temperature is selected based on a $T_m$ value of the duplex.

According to an embodiment of this invention, when the signal-generating means generates a signal in a dependent manner on the formation of a duplex, the detection temperature is controllable by adjusting a $T_m$ value of the duplex.

For example, where the signal is generated by a detection oligonucleotide specifically hybridized with the target nucleic acid sequence (e.g., Lux probe, Molecular Beacon probe, HyBeacon probe and adjacent hybridization probe), the detection of the signal is successfully done at the predetermined temperature by adjusting the $T_m$ value of the oligonucleotide. Where Scorpion primer is used, the detection of the signal is successfully done at the predetermined temperature by adjusting the $T_m$ value of a portion to be hybridized with extended strand.

Where the signal is generated by the duplex formed dependent on the presence of the target nucleic acid sequence, the detection of the signal is successfully done at the predetermined temperature by adjusting the $T_m$ value of the duplex. For example, where the signal is generated by the PTOCE method, the detection of the signal is successfully done at the predetermined temperature by adjusting the $T_m$ value of the extended duplex formed by the extension of the PTO fragment on the CTO.

The PTOCE-based methods have advantages to readily adjust $T_m$ values of the duplex or a third hybrid whose hybridization is affected by the duplex.

According to an embodiment of this invention, when the signal-generating means generates a signal in a dependent manner on cleavage of a detection oligonucleotide, the detection temperature is arbitrarily selected. In other words, any temperature can be selected so long as the signal generated by cleavage of a detection oligonucleotide may be detected. As described above, where the signal is generated being dependent manner on cleavage of the detection oligonucleotide, the label released by the cleavage may be detected at various temperatures.

The detector used in the present invention includes any means capable of detecting signals. For example, where fluorescent signals are used, photodiodes suitable in detection of the fluorescent signals may be employed as detectors. According to an embodiment, the generation of signals includes "signal generation or extinguishment" and "signal increase or decrease" from labels.

The present invention is also effective in detection of target nucleic acid sequence on a solid phase such as microarray or particles.

According to an embodiment, the signals at a relatively high detection temperature and at a relatively low detection temperature are detected on a solid phase.

According to an embodiment, the present invention is performed on the solid phase. According to an embodiment, a solid substrate where a target nucleic acid or an oligonucleotide is immobilized through its 5'-end or 3'-end onto a solid substrate is used for target detection. According to an embodiment, the oligonucleotide is hybridized with an additional oligonucleotide or a target nucleic acid. In a solid phase, the signal provided on the solid substrate is measured.

According to an embodiment, in the solid phase reaction, a single label is not required to possess the capability of generating signals different intensities depending on whether nucleic acid sequences having the single label is in a single strand or a double strand. The single label includes, but not limited to, a chemical label (e.g., biotin), an enzymatic label (e.g., alkaline phosphatase, peroxidase, β-galactosidase and β-glucosidase), a radioisotope label (e.g., $I^{125}$ and $C^{14}$), a fluorescent label, a luminescent label, a chemiluminescent label, and a metal label (e.g., gold).

For the solid phase reaction, a target nucleic acid or an oligonucleotide may be immobilized directly or indirectly through its 5'-end or 3'-end onto the surface of the solid substrate. Furthermore, a target nucleic acid or an oligonucleotide may be immobilized on the surface of the solid substrate in a covalent or non-covalent manner. Where the immobilized oligonucleotides are immobilized indirectly onto the surface of the solid substrate, suitable linkers are used. The linkers useful in this invention may include any linkers utilized for oligonucleotide immobilization on the surface of the solid substrate. For example, alkyl or aryl compounds with amine functionality, or alkyl or aryl compounds with thiol functionality serve as linkers for immobilization. In addition, poly (T) tail or poly (A) tail may serve as linkers and significantly decrease space hindrance that is an inhibitory factor to enzymatic actions (e.g., enzymatic cleavage reactions), contributing to increase in hybridization efficiency. The poly (T) tail or poly (A) tail as linker is not considered a sequence of oligonucleotides.

According to an embodiment, the oligonucleotide may be immobilized on the solid substrate via interaction between binding partners (e.g., biotin/streptavidin). For example, the oligonucleotide with one of binding partners (biotin and streptavidin) may be immobilized on the solid substrate whose surface is modified with the other binding partner.

According to an embodiment, the oligonucleotide may be immobilized on the solid substrate via a nucleotide sequence for immobilization. For example, the solid substrate whose surface is modified with the nucleotide sequence for immobilization may be used to immobilize the oligonucleotide with additional sequence complementary to the nucleotide sequence for immobilization.

According to an embodiment, the solid substrate used in the present invention is a microarray. The microarray to provide a reaction environment in this invention may include any those known to one of skill in the art. All processes of the present invention, i.e., hybridization to target nucleic acid sequences, cleavage, extension, melting and fluorescence detection, are carried out on the microarray. The immobilized oligonucleotides on the microarray serve as hybridizable array elements. The solid substrate to fabricate microarray includes, but not limited to, metals (e.g., gold, alloy of gold and copper, aluminum), metal oxide, glass, ceramic, quartz, silicon, semiconductor, Si/$SiO_2$ wafer, germanium, gallium arsenide, carbon, carbon nanotube, polymers (e.g., polystyrene, polyethylene, polypropylene and polyacrylamide), sepharose, agarose and colloids. The solid substrate may be in the form of a dipstick, a plate, a particle (e.g., bead), an affinity column and a membrane. A plurality of immobilized oligonucleotides in this invention may be immobilized on an addressable region or two or more addressable regions on a solid substrate that may comprise 2-1,000,000 addressable regions. Immobilized oligonucleotides may be fabricated to produce arrays for a given application by conventional fabrication technologies such as photolithography, ink-jetting, mechanical microspotting, and derivatives thereof.

Using confocal detection devices, the signal only on the solid substrate may be detected without influence of labels suspended in a liquid phase.

Step (b): Determining the Presence of Target Nucleic Acid Sequence

Following the detection of the signal, the presence of the target nucleic acid sequences is determined by a processed signal obtained from a difference between the signal detected at the relatively high detection temperature and the signal detected at the relatively low detection temperature.

The signals used to obtain the processed signal include that various signal characteristics from the signal detection, e.g., signal intensity [e.g., RFU (relative fluorescence unit) value or in the case of performing amplification, RFU values at a certain cycle, at selected cycles or at end-point], signal change shape (pattern) or Ct value, or values obtained by mathematically processing the characteristics.

According to an embodiment of this invention, when an amplification curve is obtained by real-time PCR, various signal values (or characteristics) from the amplification curve may be selected used to obtain the processed signal.

The signals used to obtain the processed signal in the present invention generally are a significant signal. In other words, the signals are signal to be generated being dependent on the presence of a target nucleic acid sequence. In the meantime, where the difference between the signal detected at the relatively high detection temperature and the signal detected at the relatively low detection temperature is calculated to obtain the processed signal, signal without significance such as background signals may be used to calculate the difference. In this regard, it would be understood that the signals used to obtain the processed signal encompass not only signals with significance but also signals without significance so long as they can be used to calculate the difference or involved in a determination process.

According to an embodiment, significance of signals detected may be determined using a threshold value. For example, a threshold value is predetermined from a negative control in considering background signals of detector, sensitivity or label used, and then the significance of signals from samples may be determined.

According to an embodiment of this invention, the characteristics of the signals at the relatively high detection temperature per se and the relatively low detection temperature per se may be used to obtain the difference between the signals at relatively high detection temperature and a relatively low detection temperature.

Alternatively, one or both of the signals at the relatively high detection temperature and the relatively low detection temperature may be modified by mathematically processing the characteristics of the signal and used to obtain the difference between the signals at relatively high detection temperature and a relatively low detection temperature.

According to an embodiment, where the mathematical processing is done, the characteristics of the signal should be vulnerable to the mathematical processing. In certain embodiment, the mathematical processing includes calculation (e.g., addition, multiplication, subtraction and division) using signals.

The term used herein "difference" with conjunction to signal includes not only a difference to be obtained by mathematically processing signals per se or modified signals but also a difference due to the presence and absence of signals.

According to an embodiment of this invention, the difference between the signal detected at the relatively high detection temperature and the signal detected at the relatively low detection temperature comprises a difference to be obtained by mathematically processing the signal detected at the relatively high detection temperature and the signal detected at the relatively low detection temperature.

The feature of the present method is to obtain "a processed signal" through a process to give a value reflecting the difference between signals obtained at the two detection temperatures, which is employed to qualify and quantify a target nucleic acid sequence.

The term used herein "a processed signal obtained from a difference between the signals" means signal obtained by processing both the signal detected at the relatively high detection temperature and the signal detected at the relatively low detection temperature to reflect a difference between the signals. For example, signal detected at the relatively low detection temperature and signal detected at the relatively high detection temperature are processed to give the ratio of the signals. The ratio of the signals may correspond to the processed signal (see FIG. 1A).

According to an embodiment, a point for detection of the signals (e.g., particular cycle numbers or end-point) becomes an independent variable and the processed signal becomes a dependent variable.

According to an embodiment, the mathematical processing includes calculation (e.g., addition, multiplication, subtraction and division) using signals.

The mathematical processing of the signals may be carried out by various calculation methods and their modifications.

According to an embodiment of this invention, the mathematical processing of the signals to obtain the processed signal to reflect the difference between the signals is a calculation of a ratio of the signal detected at the relatively low detection temperature to the signal detected at the relatively high detection temperature.

According to an embodiment of this invention, the mathematical processing of the signals to obtain the difference between the signals is a calculation of a ratio of the signal detected at the relatively high detection temperature to the signal detected at the relatively low detection temperature.

The term used herein "ratio" means a relationship between two numbers. By using the ratio, the presence of the target nucleic acid sequence may be determined. Where the ratio of the signal detected at the relatively low detection temperature to the signal detected at the relatively high detection temperature is significant, it becomes entitled as an indicator for the presence of the target nucleic acid sequence. For instance, where the ratio of the end-point intensity of the signal detected at the relatively low detection temperature to the end-point intensity of the signal detected at the relatively high detection temperature is significant, it indicates the presence of the target nucleic acid sequence.

According to an embodiment of this invention, the mathematical processing of the signals to obtain the processed signal to reflect the difference between the signals is a subtraction between the signal detected at the relatively low detection temperature and the signal detected at the relatively high detection temperature.

According to an embodiment of this invention, the difference between the signals may be calculated by a calculation method reflecting each detection temperature or an interval between detection temperatures or a calculation method not reflecting each detection temperature or an interval between detection temperatures.

The mathematical processing may be carried out in various fashions.

The mathematical processing may be carried out by use of a machine. For example, the signals may be undergone a mathematical processing by a processor in a detector or real-time PCR device. Alternatively, the signals may be manually undergone a mathematical processing, particularly according to a predetermined algorithm.

According to an embodiment of this invention, the method uses a negative control for determining the presence of the target nucleic acid sequence. A processed signal for the negative control may be obtained by (i) incubating a reaction mixture without a sample with a signal-generating means in a reaction vessel, (ii) detecting signals at both the relatively high detection temperature and the relatively low detection temperature, and (iii) then obtaining the processed signal from a difference between the signal detected at the relatively high detection temperature and the signal detected at the relatively low detection temperature. According to an embodiment, when the processed signal for the reaction mixture containing the sample is greater than that for the negative control, it would be determined that the sample comprises the target nucleic acid sequence. In such case, the processed signal for the negative control may be served as a threshold for determination of the presence of a target nucleic acid sequence.

According to an embodiment, where signals are generated in a real-time manner associated with target amplification by PCR, the mathematical processing of the signals comprises calculations of the ratio of a signal intensity detected at the relatively high detection temperature to a signal intensity detected at the relatively low detection temperature at each amplification cycle. The calculation results are plotted against cycles and used for determination of the presence of the target nucleic acid sequence.

According to an embodiment, where signals are generated in a real-time manner associated with target amplification by PCR, $C_t$ value is a signal used to obtain the difference.

According to an embodiment, the processed signal may be further modified to have different units or dimensions from the original signal.

According to an embodiment, the present method may be performed by detecting signals at additional at least one detection temperature as well as the two detection temperatures and determining the presence of a target nucleic acid sequence using either the signals detected at additional at least one detection temperature or between them.

According to an embodiment, the processed signal obtained from a difference between signals detected at two different temperatures may be further modified by using signals detected at other detection temperatures than the two detection temperatures or difference between them.

According to an embodiment, when signal is detected at a selected temperature at a certain cycle number or endpoint, the detections may have time intervals between detections.

According to an embodiment, the processed signal may be obtained in considering time intervals between detections at a selected detection temperature.

Detecting a target nucleic acid sequence by using two different detection temperatures enables to decrease signal variations caused by influence of reaction conditions.

According to an embodiment, the signals detected in the step (a) are signal influenced by conditions during the incubation and/or the detection, and the processed signal obtained from a difference between the signals decreases the influences of the conditions. Using the processed signal can decrease the influences of the conditions.

According to an embodiment, the signals detected in the step (a) are signal influenced by internal and/or external conditions during the incubation and/or the detection.

The term used herein "internal conditions" with conjunction to incubation (i.e., reaction) or signal detection means conditions of reactants (e.g., PCR reaction mixture) such as amount or activities components (e.g., polymerases, dNTP, primers, templates and samples). Minor variations in reaction components may have influence on a signal detected at a temperature. The term used herein "external conditions" with conjunction to incubation (i.e., reaction) or signal detection means conditions surrounding reactions for signal generation or signal detection such as thermal cycler, reaction vessel (e.g., 96-well plate) and detector. Thermal cycler conditions, small well-to-well temperature variations, deficiencies in the signal uniformity due to the instrument optical system or multiple complex optical pathways may have influence on a signal detected at a temperature.

The processed signal by the present invention contributes to decrease in influences of conditions for signal generation and/or detection, particularly, influences of external conditions.

Figure 1A:
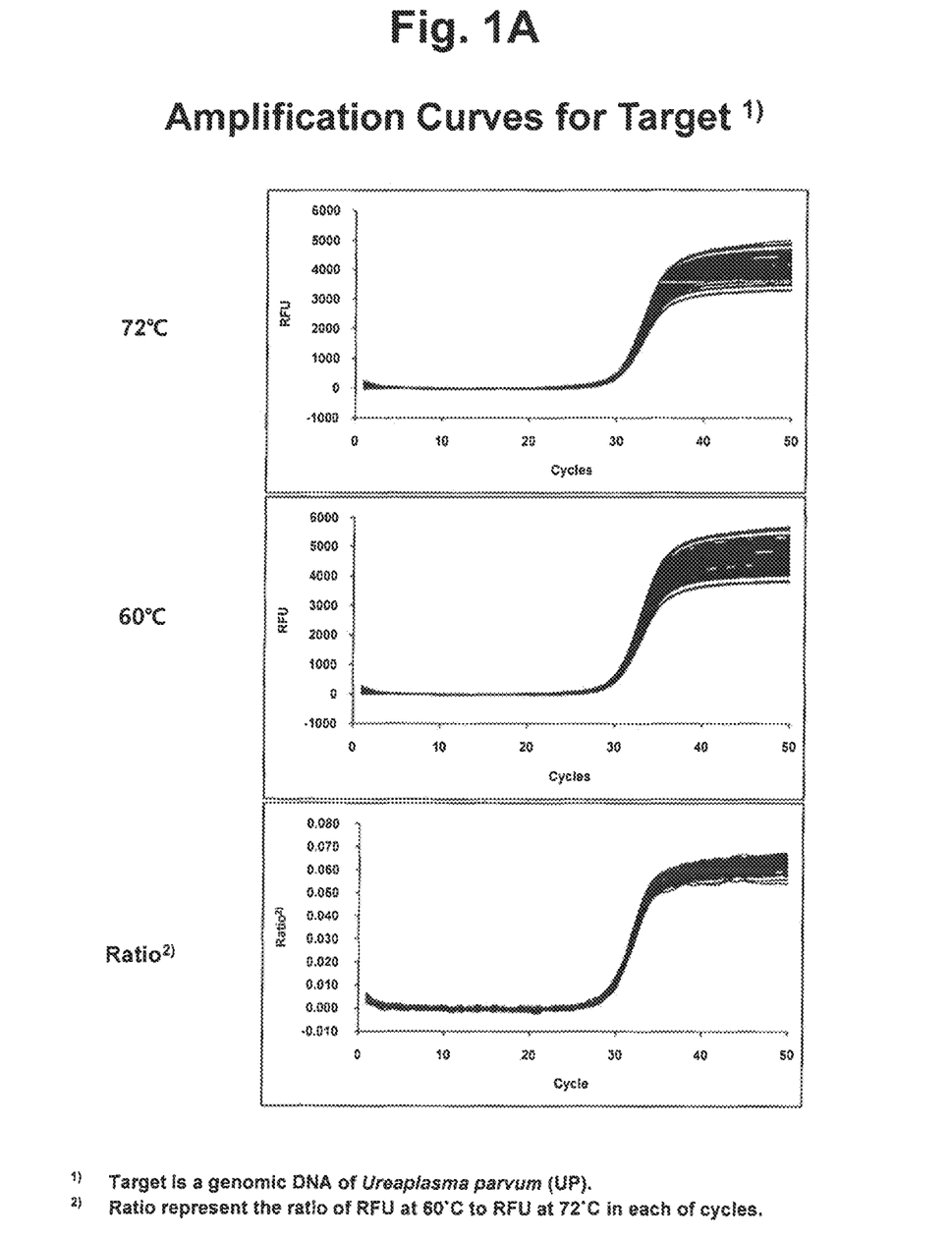
FIG. 1A represents the detection results of a single target nucleic acid sequence (genome DNA of *Ureaplasma parvum*, UP) by using signals detected at a relatively high detection temperature (72° C.), using signals detected at a relatively low detection temperature (60° C.) and using a difference (e.g., ratio) between signals detected at the two different detection temperatures (72° C. and 60° C.). The detection was performed with 96 identical reaction mixtures.

As exemplified in Example 1 and FIG. 1A, the processed signal enables to detect the target nucleic acid sequence with reduced signal variations.

According to an embodiment, the reaction mixture comprises a plurality of reaction mixtures that are prepared in accordance with the same process by using the sample.

Repetitive experiments may be done in analysis or experiments for determining the presence of a target sequence or a plurality of reaction mixtures may be used for adjustment or calibration of vessels or apparatus. The same sample is aliquoted into a multitude of reaction mixtures and then undergone real-time PCR amplification and detection under conditions that are prepared by experimenters with intention to give the same conditions for all reaction mixtures. However, signal variations are very likely to occur. The present invention ensures to decrease a signal variation between the reaction mixtures by the processed signal reflecting the difference between the signals detected at the two detection temperatures.

The processed signal reflects the difference between the signal detected at the relatively high detection temperature and the signal detected at the relatively low detection temperature, and provides results with decreased internal and external influences of reaction and detection.

The present method has effects to change in increasing or decreasing signal patterns (or shapes).

For instance, amplification curves obtained by real-time PCR detection methods using TaqMan probe show increased signal intensities upon increasing cycle number (e.g., amplification curves at 72° C. and 60° C. in FIG. 1A). Similarly, when the present invention in Example 1 uses the ratio of the fluorescence signal at 60° C. to the fluorescence signal at 72° C., an amplification curve shows increasingly the processed signal (ratio) upon increasing cycle number (ratio amplification curve in FIG. 1A). When the present invention in Example 1 uses the ratio of the fluorescence signal at 72° C. to the fluorescence signal at 60° C., an amplification curve shows decreasingly the processed signal (ratio) upon increasing cycle number. As such, the present invention may provide the same signal pattern as or contrary signal pattern to that obtained by using a single detection temperature.

Such advantage becomes more prominent in real-time PCR detection using Plexor. Amplification curves obtained by real-time PCR detection using Plexor show decreased signal intensities upon increasing cycle number (see Promega Notes 90, 2-4, 2005). Where the method is combined with the present method, an amplification curve may show increased signals upon increasing cycle number.

According to an embodiment, where signal detected at a detection temperature is shown a negative value at the end-point of reaction, a processed signal is allowed to have a positive value by the present method.

According to an embodiment, where the present method is employed to change patterns or a sign (positivity or negativity) of signal detected at a detection temperature, a relative low detection temperature is selected from a temperature to generate signal indicating the presence of a target nucleic acid sequence while a relative high detection temperature may be selected from a temperature not to generate signal indicating the presence of a target nucleic acid sequence (e.g., such temperatures can be selected when signal-generating means to generate signal by hybridization is used).

According to an embodiment of this invention, the target nucleic acid sequence comprises a nucleotide variation. The term "nucleotide variation" used herein refers to any single or multiple nucleotide substitutions, deletions or insertions in a DNA sequence at a particular location among contiguous DNA segments that are otherwise similar in sequence. Such contiguous DNA segments include a gene or any other portion of a chromosome. These nucleotide variations may be mutant or polymorphic allele variations. For example, the nucleotide variation detected in the present invention includes SNP (single nucleotide polymorphism), mutation, deletion, insertion, substitution and translocation. Exemplified nucleotide variation includes numerous variations in a human genome (e.g., variations in the MTHFR (methylenetetrahydrofolate reductase) gene), variations involved in drug resistance of pathogens and tumorigenesis-causing variations. The term nucleotide variation used herein includes any variation at a particular location in a nucleic acid sequence. In other words, the term nucleotide variation includes a wild type and its any mutant type at a particular location in a nucleic acid sequence. According to an embodiment of this invention, the nucleotide variation detected by the present invention is a SNP (single nucleotide polymorphism).

In another aspect of this invention, there is provided a computer readable storage medium containing instructions to configure a processor to perform a method for determining the presence of a target nucleic acid sequence in a sample using two different detection temperatures, the method comprising: (a) receiving both a signal detected at a relatively high detection temperature and a signal detected at a relatively low detection temperature; and (b) determining the presence of the target nucleic acid sequence by a processed signal obtained from a difference between the signal detected at the relatively high detection temperature and the signal detected at the relatively low detection temperature.

The present method described above is implemented in a processor, such as a processor in a stand-alone computer, a network attached computer or a data acquisition device such as a real-time PCR machine.

The types of the computer readable storage medium include various storage medium such as CD-R, CD-ROM, DVD, flash memory, floppy disk, hard drive, USB, magnetic tape, MINIDISC, nonvolatile memory card, EEPROM, optical disk, optical storage medium, RAM, ROM, system memory and web server.

The data (e.g., intensity, amplification cycle number and detection temperature) associated with the signals may be received through several mechanisms. For example, the data may be acquired by a processor resident in a PCR data acquiring device. The data may be provided to the processor in real time as the data is being collected, or it may be stored in a memory unit or buffer and provided to the processor after the experiment has been completed. Similarly, the data set may be provided to a separate system such as a desktop computer system via a network connection (e.g., LAN, VPN, intranet and Internet) or direct connection (e.g., USB or other direct wired or wireless connection) to the acquiring device, or provided on a portable medium such as a CD, DVD, floppy disk, portable HDD or the like to a stand-alone computer system. After the data has been received or acquired, the data analysis process proceeds to give the processed signal obtained from a difference between the signals for determination of the presence of the target nucleic acid sequence. The processor processes the received data associated with the signals to give the processed signal reflecting the difference between the signals in the two detection temperatures. For example, the processor processes the received data to obtain a ratio of the signal detected at the relatively low detection temperature to the signal detected at the relatively high detection temperature.

The instructions to configure the processor to perform the present invention may be included in a logic system. The instructions may be downloaded and stored in a memory module (e.g., hard drive or other memory such as a local or attached RAM or ROM), although the instructions can be provided on any software storage medium such as a portable HDD, USB, floppy disk, CD and DVD. A computer code for implementing the present invention may be implemented in a variety of coding languages such as C, C++, Java, Visual Basic, VBScript, JavaScript, Perl and XML. In addition, a variety of languages and protocols may be used in external and internal storage and transmission of data and commands according to the present invention.

In still another aspect of this invention, there is provided a device for detecting a target nucleic acid sequence in a sample using two different detection temperatures, comprising (a) a computer processor and (b) the computer readable storage medium of the present invention coupled to the computer processor.

According to an embodiment, the device further comprises a reaction vessel to accommodate the sample and signal-generating means, a temperature controlling means to control temperatures of the reaction vessel and/or a detector to detect signals to be generated by the signal-generating means.

According to an embodiment, the computer processor permits not only the detector to detect signals generated by the signal-generating means at a relatively high detection temperature and a relatively low detection temperature but also to calculate a difference between the signal detected at the relatively high detection temperature and the signal detected at the relatively low detection temperature. The processor may be prepared in such a manner that a single processor can do two performances: direction of detection at two detection temperatures and calculation of the difference. Alternatively, the processor unit may be prepared in such a manner that two processors do two performances, respectively.

The first essential feature of the device carries the processor to permit the device to detect signals to be generated at the two detection temperatures. According to an embodiment, where the signal is generated along with amplification of the target nucleic acid sequence, the device comprises a processor to permit the device to detect signals to be generated at the two detection temperatures at each amplification cycle.

The second essential feature of the device is to carry the processor to process the signal detected at the two detection temperatures to give the processed signal reflecting the difference between the signals. According to an embodiment, the processed signal is expressed as numeric values by a mathematical processing.

According to an embodiment, the processor may be embodied by installing software into conventional devices for detection of target nucleic acid sequences (e.g. real-time PCR device). According to an embodiment, the device comprises a processor to permit the device to detect signals at at least two detection temperatures and to mathematically process at least two detection results.

The features and advantages of this invention will be summarized as follows:

(a) The present invention using difference between signals detected at two detection temperatures enables to decrease well-to-well variation or sample-to-sample variation generated in real-time PCR processes in more convenient and effective manner.

(b) The present invention employs two different detection temperatures for detection of a target nucleic acid sequence such that the determination of the presence or quantity of a target nucleic acid sequence can be done with dramatically reduced signal variations.

(c) The detection of a target nucleic acid sequence in accordance with the present invention using difference between signals detected two detection temperatures has effects similar to calibration of target-detection devices or wells.

(d) Detection methods using a single detection temperature exhibit increased or decreased amplification curves dependent on signaling types. Interestingly, the present invention can alter patterns (or shapes) of amplification curves, such that desired patterns, particularly, increased patterns are shown.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Target Detection by Use of Difference Between Signals Detected at Two Different Temperatures We examined whether a difference of signals detected at two different temperatures can be used as a signal for target detection. Furthermore, we evaluated that the use of the difference for target detection decreases a variation of signals observed even with identical reaction mixtures.

A genomic DNA of *Ureaplasma parvum* (UP) was used as a target nucleic acid sequence. TaqMan real-time PCR was employed to detect UP. If UP is present, a TaqMan probe specifically hybridized to UP is cleaved and a labeled fragment is released. A signal from the labeled fragment can be detected theoretically at any temperatures. TaqMan probes are labeled with a fluorescent reporter molecule (FAM) at their 5'-ends and a quencher molecule at their 3'-ends (BHQ-1) (SEQ ID NO: 3). Taq DNA polymerase having a 5' nuclease activity was used for the extension of upstream primers and downstream primers, and the cleavage of TaqMan probe.

Ninety six of identical reaction mixtures were prepared and used for statistical analysis. In this Example, a "ratio" between the signals detected at two different temperatures was selected as the "difference" between the signals detected at two different temperatures for the target detection.

The sequences of upstream primer, downstream primer, and TaqMan probe used in this Example are:

```
UP-F
                                         (SEQ ID NO: 1)
5'-GCACAATTTGGATCATTAAAAGGTIIIIITGAATTCAGT-3'

UP-R
                                         (SEQ ID NO: 2)
5'-GGTTCTCAAGCAACAATATCAGCTIIIIIACCAACTTCT-3'

UP-P
                                         (SEQ ID NO: 3)
5'-[FAM]CCCAGCTATTGCACATGGTGTTGAT[BHQ-1]-3'
(I: Deoxyinosine)
```

The real-time PCR was conducted in the final volume of 20 μl containing 10 pg of UP genomic DNA, 10 pmole of upstream primer (SEQ ID NO: 1), 5 pmole of downstream primer (SEQ ID NO: 2), 3 pmole of TaqMan probe (SEQ ID NO: 3), and 10 μl of 2× Master Mix [final, 200 uM dNTPs, 2 mM $MgCl_2$, 2 U of Taq DNA polymerase (Enzynomics, Korea)]. Ninety six of identical reaction mixtures were prepared and placed in the real-time thermocycler (CFX96, Bio-Rad) for 5 min at 50° C., denatured for 15 min at 95° C. and subjected to 50 cycles of 30 sec at 95° C., 60 sec at 60° C., 30 sec at 72° C. Detection of a signal was performed at 60° C. and 72° C. of each cycle for each reaction mixture. Also, the ratio of the fluorescence signal at 60° C. to the fluorescence signal at 72° C. was calculated in each cycle for each reaction mixture. The fluorescence signals processed for calculation of the ratio were derived and exported from "No baseline subtraction" analysis data in instrumental software. The plots of fluorescence signals versus cycle number and the ratio versus cycle number for each reaction mixture were obtained with baseline subtraction respectively.

FIG. 1A shows that the presence of the target can be determined by using ratio between signals at 72° C. and 60° C. as well as by detection at a single temperature (72° C. or 60° C.). However, as shown in FIG. 1A, variations of signals were observed in even identical reaction mixtures.

Figure 1B:
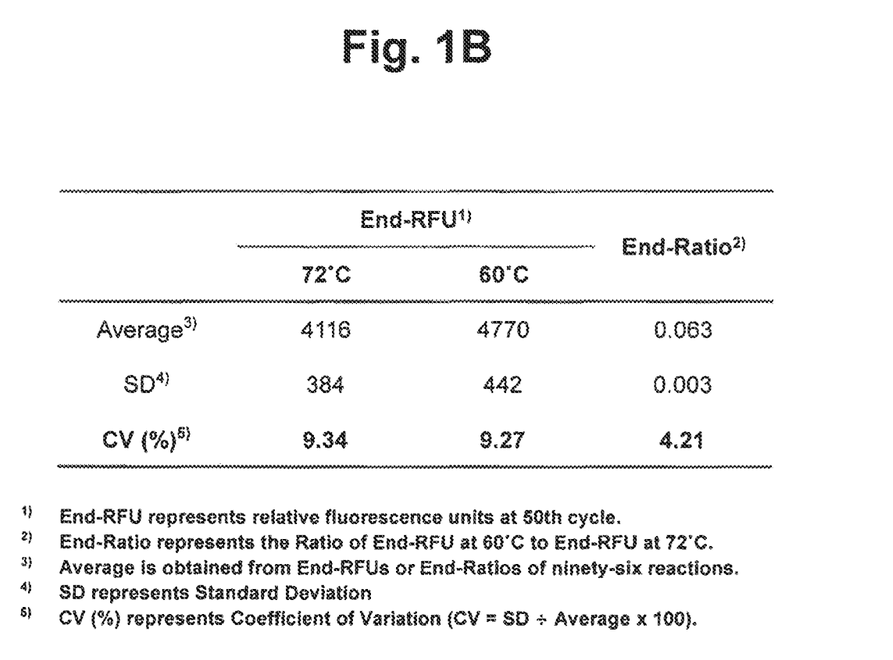
FIG. 1B shows statistical analysis results of the signal variations measured in FIG. 1A.

For comparison of signal variation depending on which types of signals are used for the target detection, the RFU values at the end cycle (End-RFU) or the ratios at the end cycle (End-Ratio) were used to calculate the average, standard variation and coefficient of variation (%) for the 96 reaction mixtures. As shown in FIG. 1B, the coefficient of variation (%) was 9.34 for 72° C. or 9.27 for 60° C. when End-RFU values detected at a single temperature were used. However, when ratios of the RFU-values detected at the two temperatures were used, the coefficient of variation (%) was decreased to 4.21.

The result of FIG. 1B shows that the present invention using a difference between signals at two different temperatures can reduce variation of the signals between independent reactions.

Example 2

Decrease in Variation of Background Signals by Use of Difference Between Signals Detected at Two Different Temperatures We examined that the use of difference between signals at two different temperatures decrease the variation of background signals.

The reaction mixture was prepared as Example 1 except that it did not contain the target nucleic acid sequence. Ninety six of identical reaction mixtures were prepared and used for the statistical analysis.

Detection of a signal was performed at 60° C. and 72° C. of each cycle for each reaction mixture. Also, the ratio of the signal at 60° C. to the signal at 72° C. was calculated in each cycle for each reaction mixture. The signals processed for calculation of the ratio were derived and exported from "No baseline subtraction" analysis data in instrumental software. The plots of background signal versus cycle number and the ratio versus cycle number for each reaction mixture were obtained respectively.

Figure 2A:
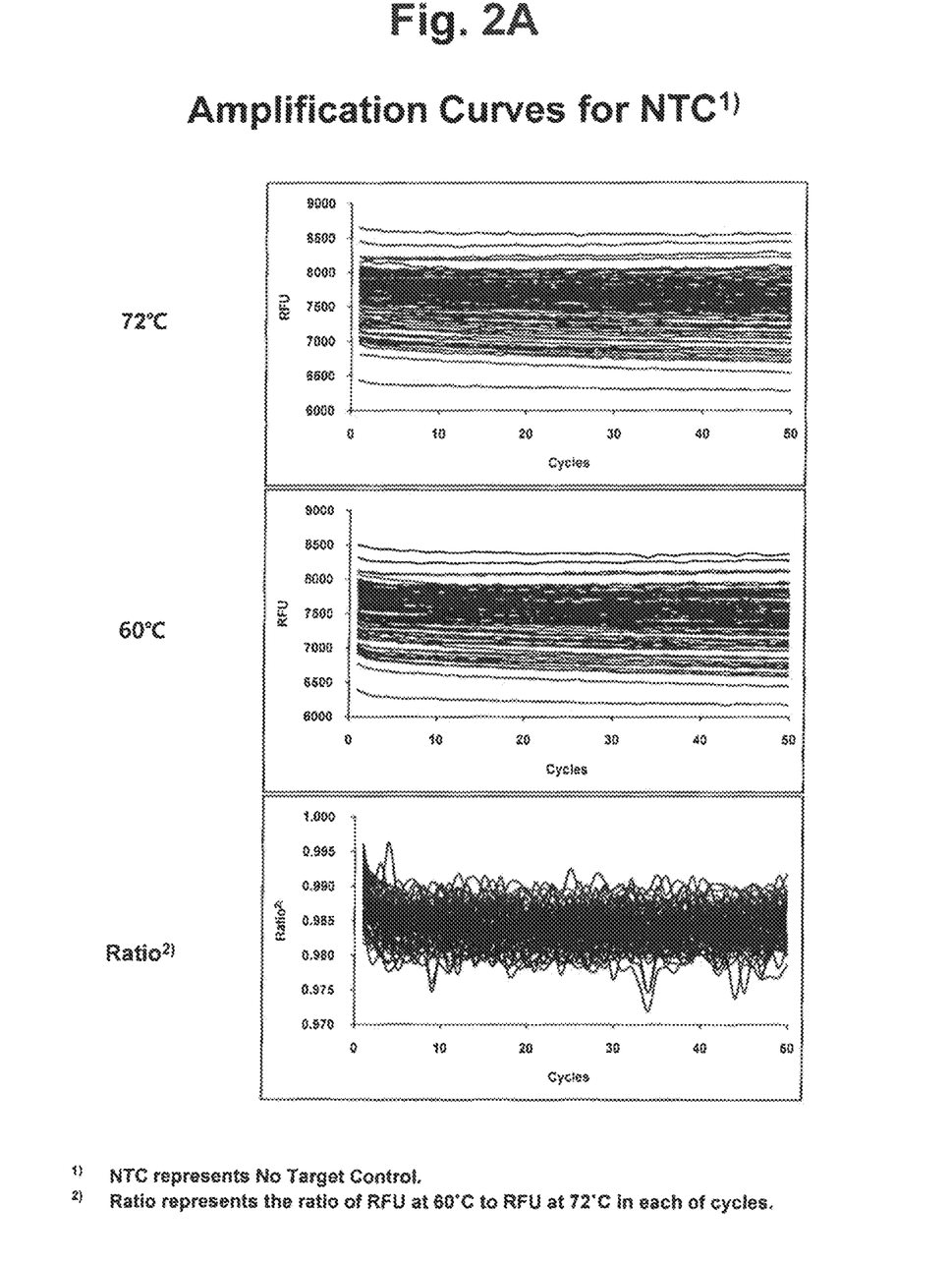
FIG. 2A represents background signals detected at a relatively high detection temperature (72° C.), background signals detected at a relatively low detection temperature (60° C.) and a processed signal obtained from the difference (e.g., ratio) between background signals detected at the two different detection temperatures (72° C. and 60° C.). The detection was performed with 96 identical no target mixtures.

As shown in FIG. 2A, variations of background signals were observed in identical reaction mixtures.

For comparison of signal variation depending on which types of signal are used, means of the RFU values (Basal-RFU) or means of the ratios (Basal-Ratio) were used to calculate the average, standard variation and coefficient of variation (%) for the 96 reaction mixtures. The RFU values of all cycles at 72° C. or 60° C. were averaged to obtain the mean of the RFU values for a reaction mixture and the ratios of all cycles for a reaction mixture were averaged to obtain the mean of the ratios for a reaction mixture.

As shown in FIG. 1B, the coefficient of variation (%) was 5.13 for 72° C. or 5.05 for 60° C. when RFU values at a single temperature were used. However, when a ratio of the RFU-values detected at the two temperatures was used, the coefficient of variation (%) was decreased to 0.23.

Figure 2B:
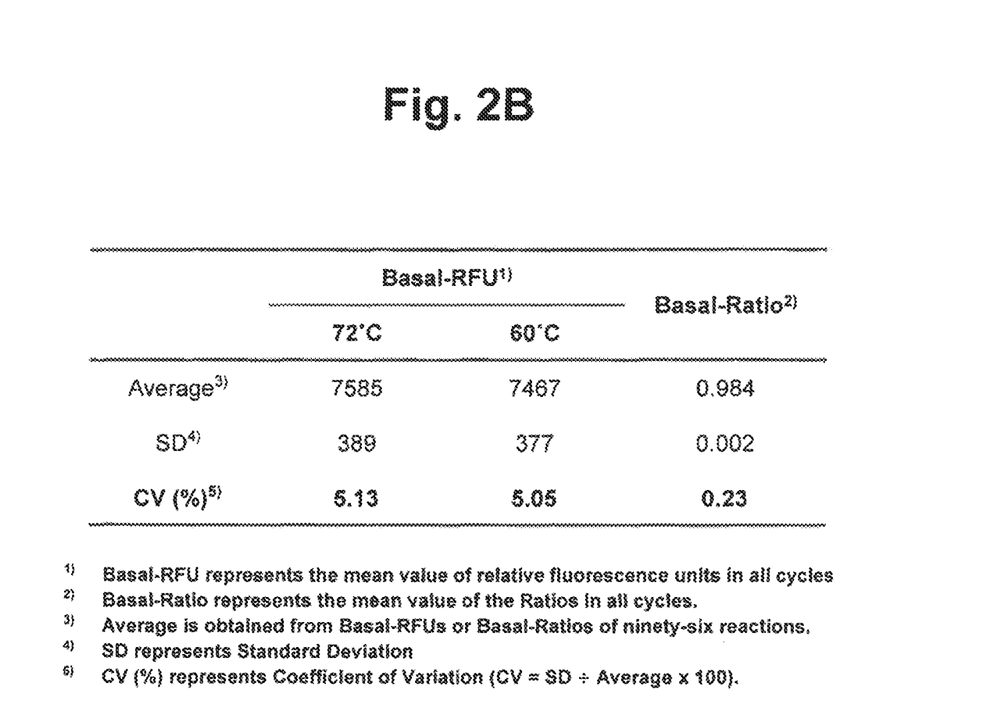
FIG. 2B shows statistical analysis results of the signal variations measured in FIG. 2A.

The result of FIG. 2B shows that the present invention using the difference between signals at two different temperatures can reduce variation of the background signals between independent reactions.

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed is:

1. A method for reducing signal variations in detecting a target nucleic acid sequence, in a sample using two different detection temperatures, comprising:
   (a) incubating a reaction mixture containing the sample and a signal-generating means for detection of the target nucleic acid sequence in a reaction vessel and detecting signals generated at a high detection temperature and at a low detection temperature; wherein the signal-generating means is a signal-generating means to generate a signal by formation of a duplex containing a detection oligonucleotide in a dependent manner on cleavage of a mediation oligonucleotide specifically hybridized with the target nucleic acid sequence or a signal-generating means to generate a signal in a dependent manner on cleavage of a detection oligonucleotide; and
   (b) determining the presence of the target nucleic acid sequence by a processed signal obtained from a difference between the signal detected at the high detection temperature and the signal detected at the low detection temperature.

2. The method according to claim 1, wherein the signals detected at the high and low detection temperatures are signals influenced by conditions during the incubation and/or the detection, and the processed signal obtained from a difference between the signals decreases the influences of the conditions.

3. The method according to claim 1, wherein the reaction mixture comprises a plurality of reaction mixtures that are prepared similarly using the sample.

4. The method according to claim 1, wherein the step (a) is performed in a signal amplification process concomitantly with a nucleic acid amplification.

5. The method according to claim 1, wherein the step (a) is performed in a signal amplification process without a nucleic acid amplification.

6. The method according to claim 1, wherein the signal-generating means is a signal-generating means to generate a signal in a dependent manner on cleavage of a detection oligonucleotide.

7. The method according to claim 1, wherein when the signal-generating means generates a signal in a dependent manner on cleavage of a detection oligonucleotide, and wherein the detection temperature is arbitrarily selected.

8. The method according to claim 1, wherein the processed signal is obtained by mathematically processing the signal detected at the high detection temperature and the signal detected at the low detection temperature for indicating the difference between the signals.

9. The method according to claim 1, wherein the signals at a high detection temperature and at a low detection temperature are detected on a solid phase.

10. The method according to claim 1, wherein the target nucleic acid sequence comprises a nucleotide variation.

11. A computer readable storage medium containing instructions to configure a processor to perform a method for reducing signal variations in determining the presence of a target nucleic acid sequence in a sample using two different detection temperatures, the method comprising:
    (a) receiving both a signal detected at a high detection temperature and a signal detected at a low detection temperature; wherein the signals are provided from a signal-generating means to generate a signal by formation of a duplex containing a detection oligonucleotide in a dependent manner on cleavage of a mediation oligonucleotide specifically hybridized with the target nucleic acid sequence or a signal-generating means to generate a signal in a dependent manner on cleavage of the detection oligonucleotide; and
    (b) determining the presence of the target nucleic acid sequence by a processed signal obtained from a difference between the signal detected at the high detection temperature and the signal detected at the low detection temperature.

12. A device for reducing signal variations in detecting a target nucleic acid sequence in a sample using two different detection temperatures, comprising:
    (a) a computer processor and
    (b) the computer readable storage medium of claim 11 coupled to the computer processor.

* * * * *